United States Patent
Pilkiewicz et al.

(10) Patent No.: US 6,793,912 B2
(45) Date of Patent: Sep. 21, 2004

(54) TREATMENT OF CANCERS BY INHALATION OF STABLE PLATINUM-CONTAINING FORMULATIONS

(75) Inventors: Frank G. Pilkiewicz, Princeton Junction, NJ (US); Joel B. Portnoff, Newtown, PA (US); Lawrence T. Boni, Monmouth Junction, NJ (US); Jin K. Lee, Belle Meade, NJ (US)

(73) Assignee: Transave Inc., Monmouth Junction, NJ (US)

( * ) Notice: Subject to any disclaimer, the term of this patent is extended or adjusted under 35 U.S.C. 154(b) by 26 days.

(21) Appl. No.: 10/224,532

(22) Filed: Aug. 20, 2002

(65) Prior Publication Data

US 2003/0078196 A1 Apr. 24, 2003

Related U.S. Application Data

(60) Provisional application No. 60/313,528, filed on Aug. 20, 2001.

(51) Int. Cl.[7] .............................. A61K 9/12; A61K 9/14

(52) U.S. Cl. .................. 424/45; 424/46; 424/489; 424/450; 514/449; 514/492; 514/908

(58) Field of Search ..................... 424/45, 46, 489, 424/450; 514/449, 492, 908

(56) References Cited

U.S. PATENT DOCUMENTS

| | | | |
|---|---|---|---|
| 4,451,447 A | 5/1984 | Kaplan et al. | 424/131 |
| 4,767,874 A | 8/1988 | Shima et al. | 556/137 |
| 5,049,388 A | 9/1991 | Knight et al. | 424/450 |
| 5,616,334 A | 4/1997 | Janoff et al. | 424/404 |
| 5,641,662 A | 6/1997 | Debs et al. | 435/172.1 |
| 5,756,353 A | 5/1998 | Debs | 435/375 |
| 5,945,122 A | 8/1999 | Abra et al. | 424/450 |
| 6,419,901 B2 | 7/2002 | Placke et al. | 424/45 |
| 6,451,784 B1 | 9/2002 | Placke et al. | 514/184 |
| 2002/0187105 A1 * | 12/2002 | Zou et al. | 424/45 |

* cited by examiner

Primary Examiner—Thurman K. Page
Assistant Examiner—Mina Haghighatian
(74) Attorney, Agent, or Firm—Foley Hoag LLP

(57) ABSTRACT

Disclosed are methods of treating cancers by inhalation of stable platinum-containing formulations.

38 Claims, No Drawings

TREATMENT OF CANCERS BY INHALATION OF STABLE PLATINUM-CONTAINING FORMULATIONS

This Application claims benefit to a provisional application No. 60/313,528 filed on Aug. 20, 2001.

The present invention relates to methods of treating cancers by administering stable platinum-containing formulations by inhalation into a subject's respiratory tract. More particularly, the present invention relates to methods of administration of cisplatin compounds by inhalation to treat lung cancers.

Cisplatin has been used for the treatment of cancers since the 1970's. It is an antineoplastic, inhibiting cell division. Cisplatin has been particularly useful in treating testicular and ovarian cancers, with good results also shown for cancers of the head and neck, esophagus, bladder, and lung. Cisplatin converts to an ineffective form in aqueous solution, consequently, cisplatin solutions must be stabilized or the drug will lose its anti-tumor effectiveness. Cisplatin is associated with several adverse side effects, including nausea and vomiting, kidney damage, and hearing loss. Previously cisplatin could only be administered by injection or infusion into a vein. The present invention, however, allows for the production and use of stable cisplatin powders, sprays, and aerosol solutions, dispersions, or liposome or liposome associated liquids, that can be administered by inhalation.

In comparison to injection or infusion, the administration of a drug by inhalation is attractive. For some cancers, inhalation can provide a more localized administration of the therapeutic agent and, therefore, can be more effective. The increased effectiveness of local administration will be seen most in the lungs and bronchial pathways, but as the platinum-containing drug is cleared from the lungs via cellular uptake and transfer to the lymphatic system, it can act on cancers affecting other areas, such as the liver, spleen, and bone marrow. With this local application approach, inhalation can reduce the side effects of cisplatin and other platinum-containing agents normally encountered after intravenous administration, due to limited bioavailability to tissues and organs via the blood stream. It can also be easier to administer therapeutics by inhalation. Cisplatin when administered intravenously is rapidly bound to various proteins found in the blood plasma, thus inactivating most of the intact platinum compound. In vivo studies indicate that this inactivation will not occur in the lung since the dose required to elicit a response in animal models is 10–100 fold more effective. Thus, the dose which is administered by inhalation can be 10–100 fold lower than the dose administered intravenously. Therefore the therapeutic index can be improved significantly. When appropriate medically, the drug can be self-administered, leading to better patient compliance and reduced cost.

Administration of therapeutic agents by inhalation does have drawbacks, however. Due to the immune response of the lung and natural breathing parameters designed to expel foreign particles, drugs that are administered by inhalation quickly clear the lung and, therefore, often yield short-term therapeutic effects since they become subject to chemical and enzymatic in-vivo degradation and/or expulsion via the airways.

The present invention can overcome the difficulties and disadvantages in current inhalation therapy and offer new advantages that can benefit the treatment of cancers by local administration. These methods minimize systemic exposure of non-cancerous cells in the body to the toxic effects of the platinum-containing drug. Less of a dose can be administered, since it is applied for local activity and is targeted to specific diseased cells in the lung rather than distributed throughout the body. The result can be an improved therapeutic index. In addition, formulations of the present invention can be prepared that will be absorbed systemically following inhalation. Such systemic absorption can occur with less toxicity. Furthermore, for some formulations, the release of the platinum can occur over a prolonged period of time.

SUMMARY OF THE INVENTION

The present invention describes novel methods of treating cancers involving inhalation of stable platinum-containing formulations. The various platinum-containing formulations are comprised of a platinum-based drug, such as cisplatin, and any stabilizers, phospholipids or liposomes, including liposomes between about 10 nm and about 1000 nm, preferably 15–300 nm, more preferably 25–100 nm, or those greater than 1 micron in diameter, preferably 2–5 microns in diameter, or polymers needed for maximum effectiveness. Additionally, when desired, the platinum-containing formulation can contain transferrin or a platinum-transferrin complex, and use carriers, such as hydrofluorocarbons or fluorochlorocarbons (including 1,1,1,2,3,3,3-heptafluoropropane, 1,1,1,2-tetrafluoroethane, dichlorodifluoromethane, trichlorofluoromethane, or 1,2-dichloro-1,1,2,2-tetrafluoroethane), and/or excipients, such as sugars, including milk sugars such as lactose.

In addition or alternatively to cisplatin, other platinum-containing drugs that may be used in the formulation include one or more of: carboplatin, oxaliplatin, iproplatin, tetraplatin, transplatin, JM118 (cis-amminedichloro(cyclohexylamine)platinum(II)), JM149 (cis-amminedichloro(cyclohexylamine)-trans-dihydroxoplatinum(IV)), JM216 (bis-acetato-cis-amminedichloro(cyclohexylamine)platinum(IV)) and JM335 (trans-amminedichloro(cyclohexylamine)dihydroxoplatinum(IV)).

A stable platinum-based formulation can be produced by milling a platinum-based drug, such as cisplatin, to a powder and combining it with sodium chloride as a dry powder blend suitable for administration by inhalation. The resulting formulation can include one or more phospholipids or liposomes. The presence of extraneous chloride ions are known to prevent the cisplatin from degrading by loss of the chloride—constituents of the cisplatin molecule when the drug is dissolved in water. The extra chloride will protect the molecule from degrading as rapidly in the presence of the moisture in the lung. The added presence of lipids or liposomes can protect against hydration, permitting adherence to the lung surface, and provide sustained contact which can allow for longer release periods.

Alternatively, the platinum-containing drug can be combined with a sodium chloride solution, then the water removed from the solution by such methods as evaporation, freeze drying or spray drying, to form sodium chloride—platinum-containing drug combination, including, but not limited to, sodium chloride crystals which protect the platinum containing—drug from degradation. These crystals can then be precipitated in such a way that they are appropriate for administration by inhalation or milled to a powder suitable for administration by inhalation.

A stable platinum-based formulation can be produced by combining cisplatin with transferrin to form a cisplatin-transferrin complex, then adding a phospholipid to produce a compound suitable for inhalation. This formulation can be combined with appropriate additives to enable it to be inhaled as a dry power, a solution, a dispersion, or a suspension.

The various platinum-containing formulations of the present invention can be administered to the subject in the form of a powder. The powder may contain one or more lipids such as phospholipids and/or excipients. The powder may be delivered to the subject's respiratory tract as an aerosol which may contain one or more sugars used as excipients. The powder may also be administered to the subject by a nebulizer.

The various platinum-containing formulations of the present invention can also be administered to the subject's respiratory tract in the form of a liquid, including liquids that contain up to about 50% ethanol, preferably about 10%, more preferably about 2–3% most preferably about 2% by weight. The liquid may be delivered to the subject as an aerosol, a nebulized spray or other sprayed composition.

In particular, the present invention describes methods of treating lung cancers by inhalation of platinum-containing formulations into the subject's respiratory tract. Lung cancers include both small cell and non-small cell primary lung cancer as well as cancers that metastasize to the lungs or the lung lymphatics. In addition, the invention describes methods of treating other cancers, such as bronchoalveolar carcinoma, leukemia, myelomas, mesotheliomas, cancers of the bronchial pathways, trachea, or esophagus, and cancers of the liver or spleen, by inhalation of a platinum-containing formulation which will be cleared from the lungs via cellular uptake and transferred to the lymphatic system.

Glossary

"Antineoplastic agent" is an agent that prevents the development, growth or proliferation of malignant cells.

"Cancer" is the uncontrolled growth of abnormal cells.

"Stable platinum-containing formulation" is a formulation containing a platinum-containing compound or ion wherein the compound or ion is stable for transformation for a time sufficient to be therapeutically useful.

"Stabilizer" is an agent that prevents or slows the transformation or deactivation of a platinum-containing compound or ion in a platinum-containing formulation.

"Subject" or "individual" is a human or animal in need of treatment for cancer.

BRIEF DESCRIPTION OF THE DRAWINGS AND TABLES

Table 1 is a tabular description of formulations for cisplatin-containing compositions to be used in the present invention.

DETAILED DESCRIPTION

The present invention is related to methods of treating cancers involving inhalation of a platinum-containing formulation. The platinum-containing formulation is inhaled into the subject's respiratory tract, where it is targeted to cancerous lesions found in the lungs or airways. It will be cleared from the lungs via cellular uptake and transferred to the lymphatic system where it may affect other cancers.

The primary advantages of the present invention over the prior art involve the benefits of inhalation therapy over injection or infusion. Previously, formulations of cisplatin were not adequately stabilized to allow administration by inhalation. Using the stabilization methods of the present invention, however, administration by inhalation is now available.

Inhalation is preferable to injection or infusion for three main reasons. First, it allows for localized administration of the antineoplastic agent to tumors of the bronchial pathways, lungs, and surrounding tissues. Localized administration has been shown to increase the effectiveness of platinum-containing drugs on other types of cancer. The therapeutic index of the drug will be greatly enhanced due to lower dose needed, systemic by-pass, and targeting to the affected cells. Second, subjects generally prefer inhalation to injection or infusion because it is less painful and will cause fewer unpleasant side effects. By avoiding wide-spread dispersion throughout the body, as occurs with intravenous use, fewer non-cancerous cells will be exposed to the toxic effects of the drug, and therefore, the subject will experience less nausea and vomiting and be at less of a risk for kidney damage or hearing loss. Third, treatment by inhalation will likely be less costly than treatment by infusion because it is easier to administer. In appropriate circumstances, subjects could receive treatment in their own homes, possibly even by self-administration.

The stabilized nature of the platinum-containing formulation should allow it to remain effective for a pharmaceutically useful period of time. Certain formulations are specially coated to adhere to the lungs and thus allow for slow release drugs to be effective.

The platinum-containing formulations are comprised of a platinum-based drug (stabilized using one of the methods detailed below), and any polymers, phospholipids or liposomes, including those 10–1000 nm in diameter, preferably those 15–100 nm in diameter and also including those greater than 1 micron in diameter and preferably 2–5 microns in diameter, needed for maximum effectiveness. Additionally, when desired, the platinum-containing formulation can contain transferrin or a platinum-transferrin complex, and use carriers, such as hydrofluorocarbons and fluorochlorocarbons (including 1,1,1,2,3,3,3-heptafluoropropane, 1,1,1,2-tetrafluoroethane, dichlorodifluoromethane, trichlorofluoromethane, or 1,2-dichloro-1,1,2,2-tetrafluoroethane), and/or excipients, such as milk sugars.

In a preferred embodiment of the invention, the platinum-containing drug is cisplatin (cis-diamminedichloroplatinum (II)).

In other embodiments, the platinum-containing drug can be one or more of: carboplatin, oxaliplatin, iproplatin, tetraplatin, transplatin, JM118 (cis-amminedichloro (cyclohexylamine)platinum(II)), JM149 (cis-amminedichloro(cyclohexylamine)-trans-dihydroxoplatinum(IV)), JM216 (bis-acetato-cis-amminedichloro(cyclohexylamine)platinum(IV)) or JM335 (trans-amminedichloro(cyclohexylamine) dihydroxoplatinum(IV)).

In an embodiment of the invention, a stable platinum-based formulation can be produced by combining cisplatin with transferrin to form a cisplatin-transferrin complex. This complex is then combined with a phospholipid to produce a stable compound suitable for administration by inhalation.

In an embodiment of the invention, a stable platinum-based formulation can be produced by combining cisplatin milled into a powder with sodium chloride as a powder blend to form a stable compound suitable for administration by inhalation.

In a preferred embodiment of the invention, a stable platinum-based formulation can be produced by dissolving a platinum-containing drug, such as cisplatin into a supersaturated solution of sodium chloride. The water from the resulting solution is then removed by such methods as evaporation, freeze drying or spray drying to produce dry sodium chloride crystals which entrap cisplatin. The crystals can then be precipitated in such a way that they are appropriate for administration by inhalation or milled to a size suitable for administration by inhalation.

Embodiments of the invention involve the method of using the platinum-containing formulation in the form of a powder or a liquid, including liquids that contain up to 50% ethanol and more preferably up to 10% ethanol, and most preferably approximately 2% ethanol. Liquids may be delivered to the subject's respiratory tract as an aerosol or a spray.

In a preferred embodiment of the invention, the platinum-containing formulation is in the form of a powder. The powder can contain excipients, including sugars, in addition to any phospholipids used for lubrication. The powder may be delivered to the subject's respiratory tract as an aerosol or by a nebulizer.

A preferred embodiment of the invention involves the method of treating lung cancers by inhalation of compounds containing cisplatin. Lung cancers include both small cell and non-small cell primary lung cancer as well as cancers that metastasize to the lungs or the lung lymphatics.

Embodiments of the invention involve the method of treating other cancers, such as leukemia, myclomas, mesotheliomas, cancers of the bronchial pathways, trachea, or esophagus, and cancers of the liver or spleen, by inhalation of platinum-containing formulations.

The dose to be administered to a subject having a cancer can be determined by a physician based on the subject's age, and physical condition, the sensitivity of the cancer to an antineoplastic agent the nature of the cancer and the stage and aggressiveness of the cancer. Generally the amount of an antineoplastic agent in a dose will be equal to or less than the corresponding dose administered intravenously. The procedures for determining cancer type and stage, sensitivity to an antineoplastic agent and the tolerated dose for a subject which can be effective in treating the cancer are well known to physicians in the field of cancer treatment.

Cisplatin-containing formulations of the present invention are shown in Table 1. These formulations when administered by inhalation can be about as effective or more effective than cisplatin delivered by infusion, and can use a lower dose of cisplatin. In addition, there can be a reduction of serious side effects experienced by a subject after receiving cisplatin administered by inhalation when compared to cisplatin administered by infusion.

For certain formulations. the lipids added to the formulations can enhance their cell kill effectiveness. For example, as the charge imparted to the formulation by the lipid becomes more negative, the formulation can become better able to disrupt cell growth. The lipids used in the formulations of the present invention can be synthetic, semi-synthetic or naturally-occurring lipids, including phospholipids, tocopherols, sterols, fatty acids, glycoproteins such as albumin, negatively-charged lipids and cationic lipids. In terms of phosholipids, they could include such lipids as egg phosphatidylcholine (EPC), egg phosphatidylglycerol (EPG), egg phosphatidylinositol (EPI), egg phosphatidylserine (EPS), phosphatidylethanolamine (EPE), and phosphatidic acid (EPA); the soya counterparts, soy phosphatidylcholine (SPC); SPG, SPS, SPI, SPE, and SPA; the hydrogenated egg and soya counterparts (e.g., HEPC, HSPC), other phospholipids made up of ester linkages of fatty acids in the 2 and 3 of glycerol positions containing chains of 12 to 26 carbon atoms and different head groups in the I position of glycerol that include choline, glycerol, inositol, serine, ethanolamine, as well as the corresponding phosphatidic acids. The chains on these fatty acids can be saturated or unsaturated, and the phospholipid may be made up of fatty acids of different chain lengths and different degrees of unsaturation. In particular, the compositions of the formulations can include DPPC, a major constituent of naturally-occurring lung surfactant. Other examples include dimyristoylphosphatidylcholine (DMPC) and dimyristoylphosphatidylglycerol (DMPG) dipalmitoylphosphatidylcholine (DPPC and dipalmitoylphosphatidylglycerol (DPPG) distearoylphosphatidylcholine (DSPC and distearoylphosphatidylglycerol (DSPG), dioleylphosphatidylethanolamine (DOPE) and mixed phospholipids like palmitoylstearoylphosphatidyl-choline (PSPC) and palmitoylstearolphosphatidylglycerol (PSPG), and single acylated phospholipids like mono-oleoyl-phosphatidylethanolamine (MOPE).

The sterols can include, cholesterol, esters of cholesterol including cholesterol hemi-succinate, salts of cholesterol including cholesterol hydrogen sulfate and cholesterol sulfate, ergosterol, esters of ergosterol including ergosterol hemi-succinate, salts of ergosterol including ergosterol hydrogen sulfate and ergosterol sulfate, lanosterol, esters of lanosterol including lanosterol hemi-succinate, salts of lanosterol including lanosterol hydrogen sulfate and lanosterol sulfate. The tocopherols can include tocopherols, esters of tocopherols including tocopherol hemi-succinates, salts of tocopherols including tocopherol hydrogen sulfates and tocopherol sulfates. The term "sterol compound" includes sterols, tocopherols and the like.

The cationic lipids used can include ammonium salts of fatty acids, phospholids and glycerides. The fatty acids include fatty acids of carbon chain lengths of 12 to 26 carbon atoms that are either saturated or unsaturated. Some specific examples include: myristylamine, palmitylamine, laurylamine and stearylamine, dilauroyl ethylphosphocholine (DLEP), dimyristoyl ethylphosphocholine (DMEP), dipalmitoyl ethylphosphocholine (DPEP) and distearoyl ethylphosphocholine (DSEP), N-(2,3-di-(9-(Z)-octadecenyloxy)-prop-1-yl-N,N,N-trimethylammonium chloride (DOTMA) and 1, 2-bis(oleoyloxy)-3-(trimethylammonio)propane (DOTAP).

The negatively-charged lipids which can be used include phosphatidyl-glycerols (PGs), phosphatidic acids (PAs), phosphatidylinositols (Pls) and the phosphatidyl serines (PSs). Examples include DMPG, DPPG, DSPG, DMPA, DPPA, DSPA, DMPI, DPPI, DSPI, DMPS, DPPS and DSPS.

Phosphatidylcholines, such as DPPC, can aid in the uptake by the cells in the lung (e.g., the alveolar macrophages) and helps to sustain release of the bioactive agent in the lung. The negatively charged lipids such as the PGs, PAs, PSs and PIs, in addition to reducing particle aggregation, are believed to play a role in the sustained release characteristics of the inhalation formulation as well as in the transport of the formulation across the lung (transcytosis) for systemic uptake. The sterol compounds are believed to affect the release characteristics of the formulation.

Preferred formulations are those which include dioleoylphosphatidyl derivatives such as DOPC, DOPE, DOPS or DOPG.

TABLE 1

AEROSOL FORMULATIONS CISPLATIN
DOSE: 0.1 mg per spray=0.1 mg per 100 mcL=0.1 mg per 0.1 ml=0.1 mg per 0.1 Gm or 1 mg/Gm
Each 10 Gm package contains 10 mg of cisplatin

| Formulation # | Cisplatin | NaCl | ETOH* | DOPG** | DOPC** | DPPG** | DPPC** | DOPS** | DOPE** | Lactose qs*** | 1,1,1,2,3,3,3, heptofluoropropane qs**** | 1,1,1,2 trifluoroethane qs**** |
|---|---|---|---|---|---|---|---|---|---|---|---|---|
| 1 | 10 mg | | | 200 mg | | | | | | 10 Gm | | |
| 2 | 10 mg | | 200 mg | 200 mg | | | | | | 10 Gm | | |
| 3 | 10 mg | | | 200 mg | | | | | | | | 10 Gm |
| 4 | 10 mg | | 200 mg | 200 mg | | | | | | | | 10 Gm |
| 5 | 10 mg | | | 100 mg | 100 mg | | | | | 10 Gm | | |
| 6 | 10 mg | | 200 mg | 100 mg | 100 mg | | | | | | | 10 Gm |
| 7 | 10 mg | | | 100 mg | 100 mg | | | | | | | 10 Gm |
| 8 | 10 mg | | 200 mg | 100 mg | 100 mg | | | | | | | 10 Gm |
| 9 | 10 mg | | | | | | | | | 10 Gm | | |
| 10 | 10 mg | | 200 mg | | | | | | | 10 Gm | | |
| 11 | 10 mg | | 200 mg | | | | | | | | | 10 Gm |
| 12 | 10 mg | | | | | 200 mg | | | | 10 Gm | | |
| 13 | 10 mg | | 200 mg | | | 200 mg | | | | 10 Gm | | |
| 14 | 10 mg | | | | | 200 mg | | | | | | 10 Gm |
| 15 | 10 mg | | 200 mg | | | 200 mg | | | | | | 10 Gm |
| 16 | 10 mg | | | | | 100 mg | 100 mg | | | 10 Gm | | |
| 17 | 10 mg | | 200 mg | | | 100 mg | 100 mg | | | 10 Gm | | |
| 18 | 10 mg | | | | | 100 mg | 100 mg | | | | | 10 Gm |
| 19 | 10 mg | | 200 mg | | | 100 mg | 100 mg | | | | | 10 Gm |
| 20 | 10 mg | | | | | | | 200 mg | | 10 Gm | | |
| 21 | 10 mg | | 200 mg | | | | | 200 mg | | 10 Gm | | |
| 22 | 10 mg | | | | | | | 200 mg | | | | 10 Gm |
| 23 | 10 mg | | 200 mg | | | | | 200 mg | | | | 10 Gm |
| 24 | 10 mg | | | | | | | 100 mg | 100 mg | 10 Gm | | |
| 25 | 10 mg | | 200 mg | | | | | 100 mg | 100 mg | | 10 Gm | 10 Gm |
| 26 | 10 mg | | | | | | | 100 mg | 100 mg | 10 Gm | | |
| 27 | 10 mg | | | 200 mg | | | | | | | 10 Gm | |
| 28 | 10 mg | | | 100 mg | 100 mg | | | | | | 10 Gm | |
| 29 | 10 mg | | | | | | | | | | 10 Gm | |
| 30 | 10 mg | | | | | 200 mg | | | | | 10 Gm | |
| 31 | 10 mg | | | | | 100 mg | 100 mg | | | | 10 Gm | |
| 32 | 10 mg | | | | | | | 200 mg | 10Gm | | | |
| 33 | 10 mg | | | | | | | 100 mg | 100 mg | | 10 Gm | |
| 34 | 10 mg | 100 mg | | 200 mg | | | | | | | 10 Gm | |
| 35 | 10 mg | 100 mg | | 100 mg | 100 mg | | | | | | 10 Gm | |
| 36 | 10 mg | 100 mg | | | | 200 mg | | | | | 10 Gm | |
| 37 | 10 mg | 100 mg | | | | 100 mg | 100 mg | | | | 10 Gm | |
| 38 | 10 mg | 100 mg | | | | | | 200 mg | | | 10Gm | |
| 39 | 10 mg | 100 mg | | | | | | 100 mg | 100 mg | | 10 Gm | |

*Range of 2–20%
**can contain 1–300 mg, preferably 100–300 mg
***Dry powder blend or spray dried/milled blend, or freeze dried/milled blend
****As aerosol dispersion in an MDI or spray dried or fine powder blend

We claim:

1. A method of treating cancer, comprising delivering via inhalation a cancer treating effective amount of a stable platinum-containing formulation to the respiratory tract of an individual in need of such treatment; wherein the stable platinum-containing formulation comprises:

(a) a milled, powder blend of cisplatin and sodium chloride, or cisplatin entrapped in sodium chloride crystals; and (b) one or more phospholipids.

2. A method of preparing a stable cisplatin-containing formulation suitable for administration by inhalation, comprising:

(a) dissolving cisplatin in a supersaturated solution of sodium chloride; and (b) removing the water from the resulting solution of (a) to produce dry sodium chloride crystals which entrap the cisplatin to form the stable cisplatin-containing composition.

3. The method of claim 2, wherein the water is removed from the solution of (b) by evaporation, freeze drying, or spray drying.

4. The method of claim 2, wherein the resulting dry crystals of (b) are milled to a size appropriate for administration by inhalation.

5. The method of claim 2, wherein the water is removed from the solution of (b) under conditions that precipitate crystals of a size appropriate for administration by inhalation.

6. The method of claim 1, wherein the stable platinum-containing formulation is produced by:

(a) milling dry cisplatin to a powder;

(b) mixing the resulting cisplatin powder of (a) with sodium chloride as a dry powder blend, resulting in the milled, powder blend; and (c) combining the milled, powder blend with one or more phospholipids to form the stable platinum-containing formulation suitable for administration by inhalation.

7. The method of claim 1, wherein the stable platinum-containing formulation comprises liposomes.

8. The method of claim 7, wherein the liposomes have an average diameter of approximately 15 to 1000 nm.

9. The method of claim 8, wherein the liposomes have an average diameter of approximately 25 to 100 nm.

10. The method of claim 7, wherein the liposomes have an average diameter of greater than 1 micron.

11. The method of claim 10, wherein the liposomes have an average diameter of 2 to 5 microns.

12. The method of claim 1, wherein the stable platinum-containing formulation comprises one or more polymers.

13. The method of claim 1, wherein the stable platinum-containing formulation further comprises one or more polymers.

14. The method of claim 1, wherein the stable platinum-containing formulation comprises a carrier.

15. The method of claim 14, wherein the carrier comprises one or more hydrofluorocarbons or fluorochlorocarbons.

16. The method of claim 15, wherein the carrier comprises one or more of: 1,1,1,2,3,3,3-heptafluoropropane, 1,1,1,2-tetrafluoroethane, dichlorodifluoromethane, trichlorofluoromethane, or 1,2-dichloro-1,1,2,2-tetrafluoroethane.

17. The method of claim 1, wherein the stable platinum-containing formulation is a powder.

18. The method of claim 17, wherein the powder is delivered to the individual's respiratory tract as an aerosol.

19. The method of claim 17, wherein the formulation comprises one or more excipients.

20. The method of claim 19, wherein the excipient comprises one or more sugars.

21. The method of claim 17, wherein the stable platinum-containing formulation is delivered to the individual's lungs by a nebulizer.

22. The method of claim 1, wherein the stable platinum-containing formulation comprises a liquid.

23. The method of claim 22, wherein the liquid includes ethanol.

24. The method of claim 22, wherein the liquid is delivered to the individual's respiratory tract as an aerosol.

25. The method of claim 22, wherein the liquid is delivered to the individul's respiratory tract as a spray.

26. The method of claim 1, wherein the cancer is a cancer that originates in the lung.

27. The method of claim 26, wherein the cancer is small cell lung cancer.

28. The method of claim 26, wherein the cancer is non-small cell lung cancer.

29. The method of claim 1, wherein the cancer is a cancer that metastasized to the lung.

30. The method of claim 1, wherein the cancer is a cancer that metastasized to the lung lymphatics.

31. The method of claim 1, wherein the cancer is a cancer that originated in the liver or spleen.

32. The method of claim 1, wherein the cancer is a cancer that is in the liver or spleen.

33. The method of claim 1, wherein the cancer is a cancer that is in the bronchus, esophagus, or trachea.

34. The method of claim 1, wherein the cancer is a cancer that is metastasized in the bronchus, esophagus, or trachea.

35. The method of claim 1, wherein the cancer is leukemia.

36. The method of claim 1, wherein the cancer is a myeloma.

37. The method of claim 1, wherein the cancer is mesothelioma.

38. The method of claim 23, wherein the stable platinum-containing formulation comprises up to 2% by weight ethanol.

* * * * *